United States Patent [19]

Orsolini

[11] Patent Number: 5,134,122
[45] Date of Patent: Jul. 28, 1992

[54] METHOD FOR PREPARING A PHARMACEUTICAL COMPOSITION IN THE FORM OF MICROPARTICLES

[75] Inventor: Piero Orsolini, Martigny, Switzerland

[73] Assignee: Debiopharm S.A., Lausanne, Switzerland

[21] Appl. No.: 555,973

[22] Filed: Jul. 20, 1990

[30] Foreign Application Priority Data

Jul. 28, 1989 [CH] Switzerland .................. 2829/89

[51] Int. Cl.$^5$ .................. A61K 37/02; C07K 5/08; C07K 5/10; C07K 7/06
[52] U.S. Cl. .................. 514/15; 424/489; 514/12; 514/13; 514/14; 514/16; 514/17; 514/18
[58] Field of Search .................. 424/489; 514/12-18

[56] References Cited

U.S. PATENT DOCUMENTS

| | | | |
|---|---|---|---|
| 4,010,125 | 3/1977 | Schally et al. | 260/8 |
| 4,107,288 | 8/1978 | Oppenheimer et al. | 424/489 |
| 4,349,530 | 9/1982 | Royer | 424/489 |
| 4,622,244 | 11/1988 | Lapka et al. | 427/213.32 |
| 4,675,189 | 6/1987 | Kent et al. | 424/490 |
| 4,767,628 | 8/1988 | Hutcison | 424/426 |
| 4,835,139 | 5/1989 | Tice et al. | 514/15 |

FOREIGN PATENT DOCUMENTS

| | | |
|---|---|---|
| 52510 | 6/1982 | European Pat. Off. . |
| 58481 | 8/1982 | European Pat. Off. . |
| 204476 | 12/1986 | European Pat. Off. . |
| 0211267 | 2/1987 | European Pat. Off. . |
| 251476 | 1/1988 | European Pat. Off. . |
| 302582 | 2/1989 | European Pat. Off. . |
| 311065 | 4/1989 | European Pat. Off. . |
| 60-181029 | 9/1985 | Japan . |
| 2209937 | 9/1989 | United Kingdom . |

OTHER PUBLICATIONS

Chang, "Biodegradable Semipermeable Microcapsules Containing Enzymes, Hormones, Vaccines and Other Biologicals", J. Bioeng. 1 (1976) p. 25.
Langer, "Controlled Release of Macromolecules", Chemtech Feb. 1982, pp. 98-105.
Hutchison et al., "Biodegradable Carriers for the Sustained Release of Polypeptides TIBTECH", Apr. 1987, (vol. 5), pp. 102-106.
M. Mason-Garcia et al., "Radioimmunoassay for Octapeptide Analogs of Somatostatin," Proc. Nat'l. Acad. Sci., vol. 85, pp. 5688-5692 (1988).

Primary Examiner—Lester L. Lee
Attorney, Agent, or Firm—Pennie & Edmonds

[57] ABSTRACT

A method for preparing a pharmaceutical composition in the form of microparticles, the composition thus obtained and its use for preparing injectable suspensions.

23 Claims, No Drawings

METHOD FOR PREPARING A PHARMACEUTICAL COMPOSITION IN THE FORM OF MICROPARTICLES

SUMMARY OF THE INVENTION

More precisely, the object of the invention is a method for preparing a pharmaceutical composition which is aimed at providing a prolonged and a controlled release of a medicamentous substance, which is obtained is the form of microparticles of a copolymer of lactic and of glycolic acids, and which incorporates, as the active substance, the pamoate, tannate, stearate or palmitate salt of a natural or of a synthetic peptide and, more particularly, of a peptide comprising 3 to 45 amino acids.

STATE OF THE ART

Various solutions have been proposed to this day for preparing compositions ensuring a prolonged and are controlled release of medicamentous substances, which are based on the preparation of biodegradable implants, on microencapsulation or on the preparation of porous biodegradable matrixes, for example in the form of microparticles of various grain sizes. In this respect, one can mention EP-A-0052510 for microencapsulation and EP-A-0058481 or U.S. Pat. No. 3,976,071 for the preparation of implants or of porous biodegradable matrixes. All these techniques make use of a preliminary dissolution in an organic solvent of the biodegradable polymer or copolymer used as support, and, when required, the dissolution of the medicamentous substance itself. Even though the dispersion of the active substance throughout the biodegradable mass is satisfactory in such cases, problems with trace amounts of residual solvent are always encountered, which may jeopardize the use of such compositions in therapeutic applications. The selection of solvents with a low toxicity or the thorough removal of traces of solvent can sometimes be complex and expensive, or it can result in an unacceptable loss of purity of the product.

It has also been proposed to dry-mix—i.e. without any solvent—a proteinic substance (Bovine Serum Albumine) and a biodegradable copolymer of lactic and of glycolic acids in the form of powders, and then to carry out a compression at the melting temperature of the mixture thus obtained (J. D. Gresser and al., Biopolymeric Controlled Release System Vol. II, p. 136). This technique did not prove satisfactory, in particular with respect to the homogeneity of the distribution of the proteinic substance (BSA) throughout the mass.

Against all expectations, it was found that these various problems could be overcome even when using as starting material the same type of biodegradable polymers or copolymers and of natural or synthetic peptides, such as octa-, nona-, or decapeptides, and more generally peptides comprising 3 to 45 amino acids, through the application of the method of the invention.

PREFERRED EMBODIMENTS OF THE INVENTION

According to the invention, natural or synthetic peptides are used in the form of salts, more precisely as pamoates, tannates, stearates or palmitates, and preferably as pamoates. It can be noted in this respect, that these salts of peptides are insoluble in water.

The above-mentioned salts, as well as the copolymers of lactic acid (L- or D,L-lactic acid) and of glycolic acid are used in the form of a powder, and more particularly, in the form of microparticles with an average grain size below approximately 200 microns. Good results were obtained with microparticles of copolymer having a grain size in the order of 180 microns or less, the peptidic salt being capable of having even a smaller grain size. The mixture of these materials is carried out by dry-mixing in any appropriate apparatus, for example in a ball mill, and at room temperature (approx. 25° C.) or even at a lower temperature, for example 5° to 10° C. The proportion of the powdered components can vary within a broad range, for example from 0.1 to 15% in weight for the peptidic salt, depending upon the therapeutic effects required.

According to the invention, once a given mixture is duly homogenized, it is subjected to a progressive compression and, simultaneously, to a progressive heating, before being extruded. These two operations, as well as the transport of the mixture to the precompression and preheating zone can be carried out advantageously using an adequately dimensioned endless screw. The compression ratio may vary depending on numerous factors, such as the geometry of the apparatus or the grain size of the powdered mixture. The control of the preheating and of the change it undergoes as the mixture progresses is more critical : depending upon the nature of the products to be treated (copolymer, peptide), every endeavour is made to maintain a temperature gradient not exceeding approximately 80° C. The initial temperature to which the powdered mixture is subjected can be 25° C., lower or higher, depending on circumstances.

The mixture thus precompressed and preheated is then subjected to an extrusion at a temperature most generally comprised between approximately 80 and 100° C, the upper limit of this range being dictated by the nature of the medicamentous substance (peptide), which should not undergo deterioration. The extrusion can be carried out at a pressure which can vary considerably in the range from 50 to 500 kg/cm$^2$, the main point being that the extrusion temperature and pressure be adapted according to the viscosity of the product. Quite obviously, an adequate pressure and an adequate temperature promote the perfect homogenization of the ingredients and, in particular, the regular distribution of the peptidic salt throughout the mass of the copolymer.

The actual extrusion is carried out by means of a nozzle of standard shape and dimensions, placed at the downstream end of the above-mentioned endless screw. The cooling of the extruded product is achieved by any appropriate means, such as cold sterile air or gas or simply through natural loss of heat.

According to the invention, the extruded product adequately cooled is then pulverized at low temperature, preferably at a temperature lower than 0° C., or even much lower, for example −10° C. or −30° C. It is advantageous to use cryogenic pulverization, a technique known per se. The product thus pulverized is then subjected to a grading of the microparticles according to their average grain size, those having a grain size below 200 microns and preferably below or equal to 180 microns being retained, in accordance with the method of the invention. The grading of the microparticles can be carried out, for example, by sieving. The graded microparticles are collected and they are then ready for use.

In accordance with the method of the invention, the steps described above take place in succession, without any excessive delay between two successive steps. An advantage of this method is that it can also be carried out as a continuous process, with all the operations taking place in succession, simply by transferring the treated mixture.

According to the invention, one can use as copolymer of lactic and glycolic acids, any type of biodegradable copolymer comprised of such a base, and preferably, a copolymer of L- or D,L-lactic acid containing respectively from 45% to 90% (moles) of lactic acid units and 55% to 10% (moles) of glycolic acid units. Such polymers are readily prepared as described in the above-mentioned literature or they can be obtained from specialized firms.

The salts of peptides, whether natural or synthetic, thus incorporated into the mass of the copolymer, are preferably salts of peptides comprising from 3 to 45 amino acids and, more particularly, salts of LH-RH (Luteinizing Hormone - Releasing Hormone), of somatostatin, of GH-RH (Growth Hormone - Releasing Hormone) or of calcitonin, or of their synthetic homologous or analogous.

More particularly, the pamoate of LH-RH, of somatostatin or of one of their homologues or analogues selected from

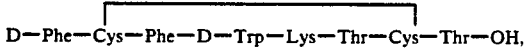

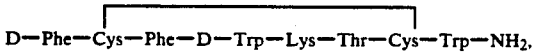

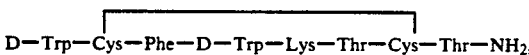

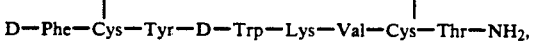

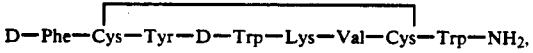

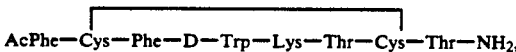

(pyro)Glu—His—Trp—Ser—Tyr—D—Trp—Leu—Arg—Pro—Gly—NH$_2$, (pyro)Glu—His—Trp—Ser—Tyr—D—Phe—Leu—Arg—Pro—Gly—NH$_2$, (pyro)Glu—His—Trp—D—Ser—Tyr—D—Leu—Leu—Arg—Pro—NHR[1] or (pyro)Glu—His—Trp—Ser—Tyr—D—Trp—Leu—Arg—Pro—NHR[1]

(R[1] lower alkyl) are concerned, this list not being limitative.

The microparticles obtained according to the method of the invention from the above-mentioned ingredients are then used, after an appropriate sterilization, for the preparation of injectable suspensions.

The following Examples illustrate the invention in a more detailed manner, without however limiting its scope.

EXAMPLE 1

20 g of a 50:50 (% moles) copolymer of D,L-lactic and glycolic acids in the form of granules having a diameter ranging approximately from 3 to 5 mm were first milled at low temperature and sieved to obtain microparticles having an average grain size of 180 microns or less.

To this powdered mass, were added 0.490g of finely pulverized pamoate of D-Trp6-LH-RH (formula of the peptide :

(pyro)Glu—His—Trp—Ser—Tyr—D—Trp—Leu—Arg—Pro—Gly—NH$_2$).

The product is comprised of microparticles with a grain size of about 10 microns and it has an amorphous structure. The resulting mixture was homogenized in a mill at room temperature.

The homogenized mixture was then placed inside an apparatus provided with an endless screw coupled to a conventional extrusion nozzle. The endless screw has a length of about 25 cm and a diameter of about 1.5 cm. It includes a first zone, the purpose of which is exclusively to move the mixture, and which neighbours a second zone designed for the compression and the preheating.

As the mixture travels, it is heated from 25° to approximately 80° C., the travelling speed being adjusted so that this phase lasts about 5 minutes. The actual extrusion takes place at 98° C., through an extrusion nozzle having an opening with a diameter of approximately 1.5 mm The filaments thus obtained are then left to cool at room temperature, cut into short portions and finally milled at −30° C. After sieving, microparticles with an average grain size of 180 microns or less are collected.

The chemical analysis, carried out on samples of the product after extrusion and milling, confirms the perfect homogeneity of the dispersion of the active substance throughout the mass of the polymer.

The microparticles obtained above were subjected to a sterilization with gamma rays and then they were suspended in an appropriate sterile vehicle. In vivo tests (determination of the level of blood testosterone in strains of male rats) confirm the regular release of the active substance during at least 25 days, which results in a fall of testosterone to castration levels.

EXAMPLE 2

Microparticles of a 50:50 (% moles) copolymer of D,L-lactic-glycolic acids were prepared according to the procedure of Example 1, to include a comparable level of pamoate of one of the following decapeptides:

(pyro) Glu—His—Trp—Ser—Tyr—D—Phe—Leu—Arg—Pro—Gly—NH$_2$, (pyro) Glu—His—Trp—D—Ser—Tyr—D—Leu—Leu—Arg—Pro—NHR$^1$ or (pyro) Glu—His—Trp—Ser—Tyr—D—Trp—Leu—Arg—Pro—NHR$^1$ ($R^1$=ethyl)

The activity tests carried out in vivo confirm a regular release of the active substance over several weeks.

EXAMPLE 3

13.85 g of a 75:25 (% moles) copolymer of D,L-lactic and glycolic acids in the form of granules with a diameter in the order of 3 to 5 mm were first milled at low temperature and sieved to obtain microparticles with an average grain size of 180 microns or less.

To this powdered mass, 1.15 g of finely pulverized pamoate of D-Trp$^6$-LH-RH (formula of the peptide:

(pyro) Glu—His—Trp—Ser—Tyr—D—Trp—Leu—Arg—Pro—Gly—NH$_2$), were added. The product consists of microcapsules with a grain size of about 10 microns and it has an amorphous structure. The resulting mixture was homogenized at room temperature in a mill, and finally subjected to the treatment described in Example 1.

After cryopulverizing, sieving and finally sterilizing with gamma rays, the microparticles were suspended in an appropriate sterile vehicle. In vivo tests (determination of the level of blood testosterone in strains of male rats) confirm the regular release of the active substance during at least 40 days, which results in a fall of testosterone to castration levels.

EXAMPLE 4

The procedure of Example 1 was followed, starting from 18 g of the 50:50 (% moles) copolymer of D,L-lactic and glycolic acids and from 2.85 g of pamoate of an analogue of somatostatin - formula of the peptide:

D—Phe—Cys—Tyr—D—Trp—Lys—Val—Cys—Trp—NH$_2$ to obtain microparticles having the desired grain size.

The chemical analysis carried out on the samples of the product after extrusion and milling, confirm the perfect homogeneity of the dispersion of the active substance throughout the mass of the copolymer.

In vivo tests further confirm the controlled release of the active substance (analogue of somatostatin) over a period of at least 7 days.

EXAMPLE 5

The procedure of Example 4 was repeated, starting this time from 13.50 g of a 75:25 copolymer of D,L-lactic-glycolic acids and from 1.50 g of pamoate of the above-mentioned analogue of somatostatin.

The microparticles thus obtained, once sterilized by means of gamma rays, were finally suspended in an appropriate sterile vehicle. In vivo tests (determination of the level of the analogue of somatostatin in blood serum of rats subjected to a single injection at $t_o$) indicate a controlled release of the active substance during at least 15 days.

EXAMPLE 6

The procedure of Example 4 was used, to obtain microparticles of a 50:50 (% moles) copolymer of D,L-lactic-glycolic acids, containing a similar amount of pamoate of one of the following octapeptides:

D—Phe—Cys—Phe—D—Trp—Lys—Thr—Cys—Thr—OH,

D—Phe—Cys—Phe—D—Trp—Lys—Thr—Cys—Trp—NH$_2$,

D—Trp—Cys—Phe—D—Trp—Lys—Thr—Cys—Thr—NH$_2$,

D—Phe—Cys—Tyr—D—Trp—Lys—Val—Cys—Thr—NH$_2$,

AcPhe—Cys—Phe—D—Trp—Lys—Thr—Cys—Thr—NH$_2$,

AcPhe—Cys—Tyr—D—Trp—Lys—Val—Cys—Trp—NH$_2$,

The chemical analysis carried out on samples of the product after extrusion and milling, confirms the perfect homogeneity of the dispersion of the active substance throughout the mass of the copolymer.

During the above-described experimentation, it was noted that the extruded filaments, once cut into short rods of an appropriate length, could be used directly as implants, after sterilization. Such implants ensure also a prolonged and a controlled release of the active substance.

What I claim is:

1. A method for preparing a pharmaceutical composition which is aimed at providing a prolonged and a controlled release of medicamentous substance, which is obtained in the form of microparticles of a copolymer of lactic and glycolic acids, and which incorporates, as the active substance, the pamoate, tannate, stearate or palmitate salt of a natural or of a synthetic peptide, characterized in that:
   a) the selected copolymer and active substance, both present in the form of microparticles whose average grain size is below approximately 200 microns, are dry-mixed in relative amounts such that the active substance is present in a proportion of about 0.1-15% by weight;
   b) the powdered mixture thus obtained is compressed and is heated up to approximately 80° C.;
   c) the precompressed and preheated mixture is subjected to an extrusion at a temperature of between approximately 80° and 100° C.; and
   d) the product resulting from the extrusion is pulverized at low temperature and then, the microparticles having a grain size below approximately 200 microns are selected and finally collected.

2. A method according to claim 1, characterized in that the microparticles of copolymer have an average grain size below or equal to 180 microns.

3. A method according to claim 2, characterized in that the precompression and the preheating of the mixture are carried out simultaneously by means of an endless screw.

4. A method according to claim 3, characterized in that the extrusion is carried out at a pressure in the range from 50 to 500 kg/cm².

5. A method according to claim 4, characterized in that the pulverization of the product resulting from the extrusion is a cryogenic pulverization.

6. A method according to claim 5, characterized in that the selection of the microparticles resulting from the pulverization is carried out by sieving.

7. A method according to claim 6, characterized in that the copolymer of lactic and glycolic acids is a copolymer of L- or D,L-lactic acid containing respectively 45 to 90% (moles) of lactic acid units and 55 to 10% (moles) of glycolic acid units.

8. A method according to claim 7, characterized in that the active substance is the pamoate, tannate, stearate or palmitate of a natural or of a synthetic peptide comprising 3 to 45 amino acids, and including LH-RH, somatostatin, GH-RH, calcitonin or one of their synthetic analogues or homologues.

9. A method according to claim 8, characterized in that the active substance is a pamoate of LH-RH, of somatostatin or of one of their analogues or homologues selected from

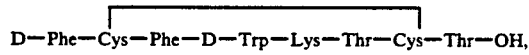

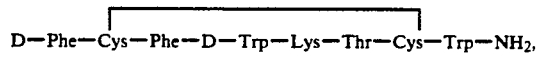

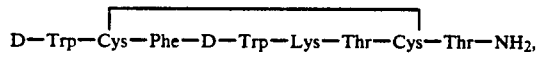

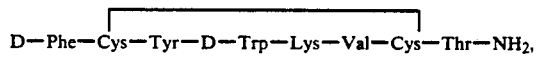

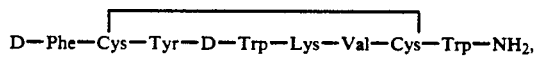

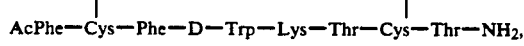

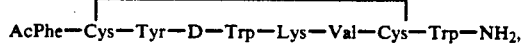

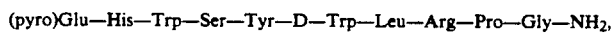

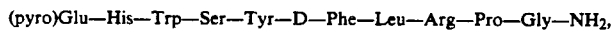

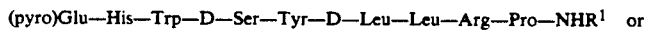    or

($R^1$ = lower alkyl).

10. A method for preparing a pharmaceutical composition which provides a prolonged and controlled release of an active substance, which comprises:
   a) mixing microparticles of a copolymer of lactic and glycolic acids with microparticles of an active substance of an insoluble salt of a natural or synthetic peptide comprising 3 to 45 amino acids for a sufficient time to form a homogenous mixture containing about 0.1 to 15% by weight of the active substance, each of said microparticles having an average grain size of below approximately 200 microns; and
   b) precompressing and preheating the mixture prior to extruding the precompressed and preheated mixture at a temperature of between approximately 80° and 100° C. to form a product for use as said pharmaceutical composition.

11. A method according to claim 10 which further comprises:

c) pulverizing the extruded product at low temperature; and
d) selecting the microparticles which have a grain size of below about 200 microns for use as said pharmaceutical composition.

12. A method according to claim 11 which further comprises selecting the microparticles of the copolymer to have an average grain size of 180 microns or less.

13. A method according to claim 11 wherein the precompressing and preheating of the mixture are carried out simultaneously by passing the mixture through an endless screw.

14. A method according to claim 11 wherein the extrusion is carried out at a pressure in the range of about 50 to 500 kg/cm².

15. A method according to claim 11 which further comprises pulverizing the extruded product at cryogenic temperatures.

16. A method according to claim 11 wherein the selection of the microparticles for use as the pharmaceutical composition is obtained by sieving the desired grain size of the pulverized product.

17. A method according to claim 11 which further comprises selecting the copolymer of lactic and glycolic acids to be a copolymer of L- or D,L-lactic acid containing 45 to 90% (moles) of lactic acid units and 55 to 10% (moles) of glycolic acid units.

18. A method according to claim 11 which further comprises selecting the active substance to be a pamoate, tannate, stearate or palmitate salt of LH-RH, somatostatin, GH-RH, calcitonin or a synthetic analogue or homologue thereof.

19. A method according to claim 11 which further comprises selecting the active substance to be a pamoate salt of LH-RH, somatostatin or an analogue or homologue thereof selected from the group consisting of:

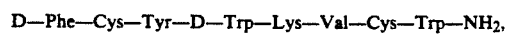

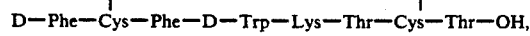

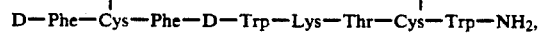

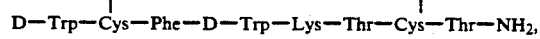

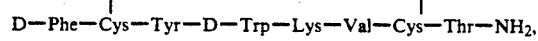

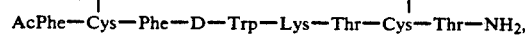

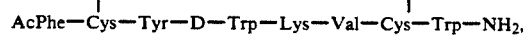

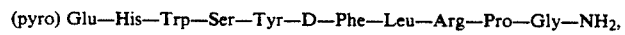

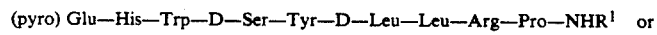

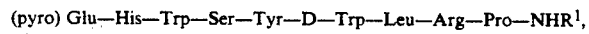

where $R^1$ = a lower alkyl group.

20. The method of claim 1 wherein additional heat and pressure are simultaneously applied in slowly increasing amounts to the powdered mixture of the selected copolymer and active substance.

21. The method of claim 20 wherein additional heat and pressure are simultaneously applied in slowly increasing amounts to the powdered mixture of the selected copolymer and active substance as the mixture is transported in an endless screw.

22. The method of claim 10 wherein additional heat and pressure are simultaneously applied in slowly increasing amounts to the powdered mixture of the selected copolymer and active substance.

23. The method of claim 22 wherein additional heat and pressure are simultaneously applied in slowly increasing amounts to the powdered mixture of the selected copolymer and active substance as the mixture is transported in an endless screw.

* * * * *